United States Patent [19]

Gupton et al.

[11] Patent Number: 4,902,819
[45] Date of Patent: Feb. 20, 1990

[54] PREPARATION OF SODIUM DIETHYL OXALACETATE

[75] Inventors: B. Franklin Gupton, Virginia Beach; James H. Rae, Portsmouth, both of Va.

[73] Assignee: Hoechst Celanese Corporation, Somerville, N.J.

[21] Appl. No.: 247,496

[22] Filed: Sep. 22, 1988

Related U.S. Application Data

[63] Continuation-in-part of Ser. No. 94,413, Sep. 9, 1987, abandoned.

[51] Int. Cl.$^4$ ............................................. C07C 69/732
[52] U.S. Cl. ..................................................... 560/181
[58] Field of Search ......................................... 560/181

[56] References Cited

U.S. PATENT DOCUMENTS 1,948,201  2/1934  Carter et al. .................... 560/181

OTHER PUBLICATIONS

Puncochar et al., Chemical Abstracts, vol. 98, No. 215194a (1983).
Rossi et al., Chemical Abstracts, vol. 42, No. 4937i (1948).

*Primary Examiner*—Bruce Gray
*Attorney, Agent, or Firm*—Depaoli & O'Brien

[57] ABSTRACT

Sodium diethyl oxalacetate is prepared in a specific manner by adding sodium ethoxide to a mixture of diethyl oxalate and ethyl acetate to obtain a free flowing sodium salt which is easily separable and purified.

6 Claims, No Drawings

PREPARATION OF SODIUM DIETHYL OXALACETATE

CROSS-REFERENCE TO RELATED APPLICATIONS

This application is a Continuation-in-Part of Ser. No. 094,413, filed Sept. 9, 1987 now abandoned.

FIELD OF THE INVENTION

The present invention relates to an improved process for the production of carboxylic acid esters. More particularly, the invention relates to a simplified and efficient process for the preparation of sodium diethyl oxalacetate by condensing diethyl oxalate and ethyl acetatein the presence of sodium ethoxide in a specific manner.

DESCRIPTION OF THE PRIOR ART

The sodium salt of diethyl oxalacetate is a stable material which finds utility in the synthesis of pyrazolone derivatives, as an intermediate in the preparation of dyes and medicinal products, and more recently in the preparation of herbicides. Salts of this type and their preparation are disclosed in U.S. Pat. No. 1,948,201 in which metallic sodium is dissolved in ethanol to form sodium ethylate, after which the solution is cooled to 0° C.–15° C. and stoichiometric amounts of diethyl oxalate and ethyl acetate are added thereto. The reaction is allowed to proceed for a period of 2–4 hours at 0° to 15° C. and the reaction mixture is then boiled for 15 to 30 minutes, cooled, and thereafter filtered to recover a cake of sodium ethyl oxalacetate. A similar preparation is disclosed in Czechoslovakian Patent application No. 5,359-78 dated Aug. 17, 1978. When producing sodium diethyl oxalacetate by either of these prior art processes, however, the diethyl oxalate and ethyl acetate reactants are added to the sodium ethoxide and, as a result, it has been found that the product mixture sets up firmly in the ractor and becomes almost impossible to vacuum filter. Even when the product mixture is slurried in a large excess of alcohol the problem becomes further multiplied since the slurry severely clogs the filters and special consideration is required for cleaning the filters and/or disposal of the slurry. The prior art processes thus suffer from a number of disadvantages and, accordingly, there is a need for an improved process for preparing sodium diethyl oxalacetate.

SUMMARY OF THE INVENTION

The present invention is directed to solving the aforementioned problems and has for its object to provide a simple and efficient process for producing the sodium salt of diethyl oxalacetate with little or no handling problems. It has been found that the disadvantages of the prior art methods are overcome by adding sodium ethoxide to a reaction mixture of diethyl oxalate and ethyl acetate rather than producing the sodium salt by adding the oxalate and acetate to the ethoxide. Surprisingly, this reverse addition of reactants, followed by conventional cooling and heating procedures, has been found to eliminate the time consuming, costly, and inefficient methods of the prior art which are unacceptable for producing sodium diethyl oxalacetate on a production scale basis.

DETAILED DESCRIPTION OF THE INVENTION

In carrying out the method of the invention a mixture of diethyl oxalate and ethyl acetate is charged to a suitable reactor in which the contents of the reactor are cooled to a temperature within the range of 0° C. to 40° C., preferably about 0° C. to 15° C. Sodium ethoxide, is added at a rate and temperature which will maintain a reaction temperature of 0° C. to 15° C. The reaction is carried out with stirring for at least 2 hours, preferably about 4 hours, at temperatures of 15° C. or less, e.g., 5° C. to 15° C.

The amount of sodium ethoxide, diethyl oxalate, and ethyl acetate used in the condensation reaction can vary somewhat but it is preferred to use substantially stoichiometric amounts of each reactant. Good results have been obtained and sodium diethyl oxalacetate can be produced easily with a good yield by using equimolar amounts of each reactant according to the following equation:

$$CH_3-\underset{\underset{O}{\|}}{C}-OC_2H_5 + C_2H_5-O-\underset{\underset{O}{\|}}{C}-\underset{\underset{O}{\|}}{C}-OC_2H_5 + \qquad I.$$

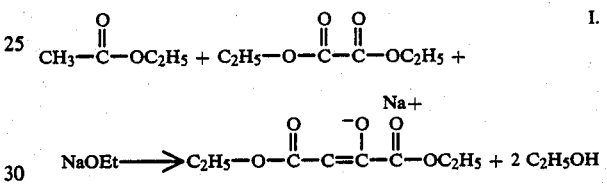

$$NaOEt \longrightarrow C_2H_5-O-\underset{\underset{O}{\|}}{C}=\underset{\underset{-O}{|}}{C}-\underset{\underset{O}{\|}}{C}-OC_2H_5 \overset{Na+}{} + 2\ C_2H_5OH$$

It has been found desirable to employ an organic solvent to dissolve the sodium ethoxide reactant before entering the reaction zone. Any solvent which would react with the charge components should, of course, be avoided. Suitable solvents include saturated aliphatic lower alkanols of 2 to 6 carbon atoms, such as ethanol, propanol, butanol, etc., and aromatic hydrocarbons having between 1 and 3 aromatic rings and between 6 and 18 carbon atoms per molecule. Suitable specific examples of aromatic solvents include, for example, benzene, toluene or xylene. The sodium ethoxide ingredient is preferably dissolved in ethanol to provide a concentration ranging from about 18 to 21 weight percent. Good yields are obtained in a reasonable time when using a concentration of about 19.5 weight percent.

Upon completion of the cold cycle, the reaction mixture is quickly raised to a temperature of 70° C. to 80° C., preferably about 75° C., to complete the condensation and to promote deprotonization. This can be accomplished in a short period of time, usually in one-half hour or less, by heating the reaction mixture to reflux. The contents of the reactor are then allowed to cool at which time the product resembles a yellowish paste. The solids are suitably filtered, by centrifuging, vacuum filtration, or the like, and then conventionally washed with ethanol and dried.

The temperature of this final cooling step is not critical and can vary over a fairly wide temperature range. The temperatures of the preceding steps, i.e., the cold cycle and the completion of the condensation, are critical.

The final cooling is conveniently carried out at room temperature which varies from about 20°–40° C. depending on such art-recognized factors as location, time of year, etc.

The inventions will be further described by reference to the following examples which illustrate the best mode now contemplated for carrying out the invention.

EXAMPLE 1

A mixture of 150 grams of freshly distilled diethyl oxalate and 91.1 grams of ethyl acetate was added to a two liter reaction kettle which was fitted with a mechanical stirrer, addition funnel, thermometer and thermowatch. The contents of the kettle were cooled to 0° C.–15° C. by means of an ice bath. 325 grams of a 21% solution of sodium ethoxide in ethanol were then added dropwise into the kettle. The mixture was stirred mechanically during the addition. After 4 hours of stirring, the ice bath was removed and the reaction kettle was heated to gentle reflux for 30 minutes and then allowed to cool down to room temperature, e.g., about 20° C., at which time the contents of the kettle resembled a paste. The solid material was filtered by vacuum filtration, washed with a large volume of ethanol, filtered, and dried without heat for 1½ days. The solid material, which weighed 158.0 grams, was then crushed to a finely divided powder with mortar and pestle, placed in an evaporating dish and vacuum dried in an oven. The product was additionally dried using full vacuum at 60° C. for 6 hours to yield 153.30 grams of a free flowing crystalline product which was identified by gas chromatograph as the sodium salt of diethyl oxalacetate.

EXAMPLE 2

In this experiment the procedure of Example 1 was followed except that a reverse order of addition was carried out, i.e., 325 grams of a 21% solution of sodium ethoxide in ethanol was added to the pot, and 91 grams of ethyl acetate and 150 grams of diethyl oxalate were mixed in the addition funnel and added dropwise to the pot over a period of 25 minutes at a temperature of 0° C. to 15° C. The mixture was stirred at 0° C.–15° C. for 4 hours during which time the contents of the pot became opaque and reddish brown solids were formed. The ice bath was removed and the reaction mixture was heated to reflux (80° C.) for 30 minutes and then allowed to cool down to room temperature, e.g., about 20° C. When heating to reflux, smoking and the evolution of gas occurred at 50° C. During the cool down period the reaction mixture set up firmly in the pot and had to be slurried with 500 ml of ethanol. Vacuum filtration of the slurry was almost impossible and after 4 hours the slurry was left to filter overnight. After drying, 152.19 grams of the sodium salt of diethyl oxalacetate were recovered.

EXAMPLE 3

Example 2 was repeated and to aid crystallization, 0.2 grams of solid sodium diethyl oxalacetate seeds were added at 45° C. during the cool down period. Three minutes after addition of the seeds, solids began to form. The pot was cooled with an ice bath and rapid formation of solids began. The pot was stirred at close to maximum speed for fifteen minutes and then filtered. When an attempt was made to filter the product slurry, the filter became clogged and after three hours the experiment was terminated. The filter was cleaned and the slurry was sent to disposal.

What is claimed is:

1. In a method of preparing sodium diethyl oxalacetate by reaction of sodium ethoxide, diethyl oxalate and ethyl acetate, the improvement which comprises adding sodium ethoxide to a mixture of diethyl oxalate and ethyl acetate while maintaining a temperature of about 0° C. to 40° C., reacting said ethoxide, oxalate and acetate mixture for a period of time sufficient to obtain a product mixture containing sodium diethyl oxalacetate, heating the product mixture to a temperature of 70° C. to 80° C. for a period of time ranging from ¼ to 2 hours, cooling the product mixture to room temperature, and thereafter recovering sodium diethyloxalacetate.

2. The method of claim 1 wherein the sodium ethoxide is added as an 18 to 21 wt % solution in ethanol.

3. The method of claim 2 wherein the sodium ethoxide is added to the mixture of diethyl oxalate and ethyl acetate at a temperature of 0° C. to 15° C.

4. The method of claim 3 wherein the ethoxide, oxalate and acetate mixture is stirred for 4 hours at a temperature of 5° C. to 15° C.

5. The method of claim 4 wherein the product mixture is heated to 75° C. for about ½ hour.

6. A method of preparing sodium diethyl oxalate which comprises forming a reaction mixture by adding an 18 to 21 wt % solution of sodium ethoxide in ethanol to substantially stoichiometric amounts of diethyl oxalate and ethyl acetate while maintaining a temperature of about 5° C. to 10° C., stirring the reaction mixture for about 4 hours at a temperature of about 5° C. to 15° C. to obtain a product mixture containing sodium diethyl oxalacetate, heating the product mixture to 75° C. for about ½ hour, cooling the product mixture to room temperature, subjecting the slurry to centrifugation to obtain sodium diethyl oxalacetate crystals, and thereafter washing the crystals with ethanol to recover a purified product.

* * * * *